US007030105B2

(12) United States Patent
Brasch et al.

(10) Patent No.: US 7,030,105 B2
(45) Date of Patent: Apr. 18, 2006

(54) METHOD OF SYNTHESIS OF β-THIOLATO COBALAMIN COMPOUNDS

(75) Inventors: Nicola E. Brasch, Kent, OH (US); Ling Xia, Kaleen (AU)

(73) Assignee: Kent State University, Kent, OH (US)

( * ) Notice: Subject to any disclaimer, the term of this patent is extended or adjusted under 35 U.S.C. 154(b) by 312 days.

(21) Appl. No.: 10/430,468

(22) Filed: May 6, 2003

(65) Prior Publication Data

US 2004/0054128 A1 Mar. 18, 2004

Related U.S. Application Data

(60) Provisional application No. 60/379,354, filed on May 8, 2002.

(51) Int. Cl.
*A61K 31/40* (2006.01)
*A61K 31/155* (2006.01)
*A61B 5/055* (2006.01)
*A61B 10/00* (2006.01)
*C07B 47/00* (2006.01)

(52) U.S. Cl. .................. 514/185; 424/9.362; 424/9.61; 540/145; 534/15; 514/410

(58) Field of Classification Search ............. 424/9.362, 424/9.61; 540/145; 534/15; 514/185, 410
See application file for complete search history.

(56) References Cited

U.S. PATENT DOCUMENTS 3,146,165 A * 8/1964 Heathcote .................... 514/52

OTHER PUBLICATIONS

Shargel et al. Comprehensive Pharmacy Review. 4th Edition.Lippincott Williams & Wilkins. 2001. pp. 54-57, 99-100.*
Gennaro et al. Remington: The Science and Practice of Pharmacy. 19th edition. Philadelphia College of Pharmacy and Science. 1995. pp. 631-634.*
Article from *Journal of the American Chemical Society/* 88:21/Nov. 5, 1966, pp. 5018-5019, entitled Reaction of Hydroxocobalamin with Thiols; Norman Adler, Thomas Medwick, and T. J. Poznanski.
Vol. 169, No. 2, 1990, Jun. 2, 1990; pp. 443-450; *Biochemical and Biophysical Research Communications*; Ewa Pezacka, Ralph Green and Donald W. Jacobsen.
Article Biochemistry 1993, 32, 8421-8428; *Heteronuclear Nuclear Magnetic Resonance Studies of Cobalt Corrinoids. 15. The Structure of Glutathionylcobalamin: A¹H and ¹³C Two-Dimensional Nuclear Magnetic Resonance Study at 600 MHz†* Kenneth L. Brown and Xiang Zou; Department of Chemistry, Box CH, Mississippi State University, Mississippi State, Mississippi 39762; Susan R. Sabon and Donald W. Jacobsen; Department of Cell Biology and Clinical Pathology, The Cleveland Clinic Foundation , Cleveland, OH 44106; Received Mar. 12, 1993; Revised Manuscript Received May 6, 1993.
Article from *Journal of Inorganic Biochemistry* 76 (1999) 197-209pp. 197-209; entitled "*Synthesis and characterization of isolable thiolatocobalamin complexes relevant to coenzyme $B_{12}$ -dependent ribonucleoside triphosphate reductase*" Nicola E. Brasch, Twui-Ling Carolyn Hsu, Kenneth M. Doll, Richard G. Finke, Department of Chemistry, Colorado State University, Fort Collins, CO 80523; Received Mar. 5, 1999; received in revised form Aug. 2, 1999; accepted Aug. 16, 1999.
*Inorganic Chemistry* vol. 40, No. 12, 2001; pp. 2686-2692; "*Synthesis, Characterization, Solution Stability, and X-ray Crystal Structure of the Thiolatocobalamin γ-Glutamylcysteinylcobalamin, a Dipeptide Analogue of Glutamylcysteinylcobalamin: Insights into the Enhanced Co—S Bond Stability of the Natural Product Glutamylcysteinylcobalamin*"; Robert K. Suto, † Nicola E. Brasch, ‡,§ Oren P. Anderson,‡ and Richard G. Finke*,‡ Departments of Biochemistry and Chemistry, Colorado State University, Fort Collins, CO 80523; Received Dec. 6, 2000.

* cited by examiner

*Primary Examiner*—James O. Wilson
*Assistant Examiner*—Matthew L. Fedowitz
(74) *Attorney, Agent, or Firm*—Hudak, Shunk & Farine CO LPA

(57) ABSTRACT

The invention provides a method for preparing glutathionylcobalamin (GluSCbl) which involves running the reaction in an aqueous solvent with a relatively small excess of glutathione, i.e. GluSH, specifically from one to less than four molar equivalents of GluSH. The formed GluSCbl is precipitated from the aqueous solvent, preferably by the addition of a precipitate inducing solvent. This provides GluSCbl in acceptable purity without the need for an additional chromatographic purification step. Additionally, it has been found that the reaction can be run to an acceptable level of purity by using very high concentrations of the reactants, i.e. around saturation concentrations for aquocobalamin. This has the advantage of eliminating the need for air-free conditions.

18 Claims, No Drawings

METHOD OF SYNTHESIS OF β-THIOLATO COBALAMIN COMPOUNDS

This Patent Application is Based Upon U.S. Provisional Application Ser. No. 60/379,354 Filed May 8, 2002

FIELD OF THE INVENTION

The present invention relates generally to the preparation of thiol-containing cobalamin compounds, or thiolatocobalamins. In particular, the invention relates to methods for the preparation of thiolatocobalamins such as glutathionylcobalamin, which provide a high purity product without the need for additional chromatographic purification steps and further which do not require synthesis under air-free conditions.

BACKGROUND

There are approximately fifteen enzyme reactions known which require one of the two coenzyme forms of vitamin $B_{12}$ to function. Two of these enzymes, methionine synthase and methylmalonyl-coenzyme A mutase, occur in humans (Dolphin, D. (ed.) $B_{12}$; John Wiley & Sons, Inc.: New York, USA, 1982; Banerjee, R. (ed.) *Chemistry and Biochemistry of $B_{12}$*; John Wiley & Sons, Inc.: New York, USA, 1999). The $B_{12}$-dependent enzyme reactions play a vital role in maintaining healthy nerve and red blood cells and are required for the synthesis of DNA. Formula (I) depicts the structure of vitamin $B_{12}$ ($X=CN^-$, cyanocobalamin) and its derivatives, commonly referred to as the cobalamins. The α (or lower) axial site is occupied by an intramolecularly-bound 5,6-dimethylbenzimidazole, and the β (or upper) axial site can be occupied by a variety of ligands. The cobalamins belong to a family of compounds known as the corrinoids, which differ from one another in the specific nucleotide occupying the α axial site of the cobalt corrin complex.

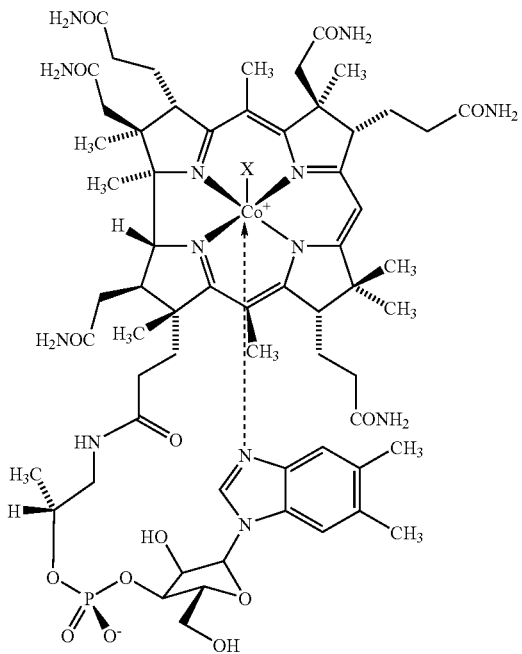

(I) $X=CN^-$ cyanocobalamin (vitamin $B_{12}$)
(II) $X=H_2O/OH^-$ aquocobalamin/hydroxycobalamin
(III) $X=CH_3$ methylcobalamin
(IV) $X=5'$-deoxyadenosyl (adenosylcobalamin, coenzyme $B_{12}$)
(V) $X=$glutathione (glutathionylcobalamin)

Three forms of vitamin $B_{12}$ have long been recognised to occur in biology, aquocobalamin/hydroxycobalamin (II), methylcobalamin ($CH_3Cbl$) (III) and adenosylcobalamin (AdoCbl) (IV) (Golding, B. T. *Chem. Brit.* 1990, 950). The latter two forms play a crucial role in the $B_{12}$-dependent enzyme reactions, and are frequently referred to as the $B_{12}$ coenzymes. Severe $B_{12}$-deficiency may lead to megoblastic anaemia and/or neurological impairment. Insufficient vitamin $B_{12}$ as a result of faulty absorption frequently manifests as pernicious anaemia. $B_{12}$-related conditions arising from malabsorption can be easily (and reversibly) treated by administering vitamin $B_{12}$ (I) or its hydroxycobalamin derivative (II), either orally or by injection into muscle tissue.

Recently, other therapeutic applications have been identified. McCaddon and co-workers have proposed that glutathionylcobalamin (GluSCbl) (V) may be an effective therapeutic for the treatment of Alzheimer's disease (AD) and other neurological diseases (McCaddon, A.; Regland, Bjorn; Hudson, P.; Davies, G. *Neurol.* 2002, 58, 1395–1399). It is now generally accepted that "oxidative stress" is an important neurodegenerative element in AD and several other neurological diseases. Glutathionylcobalamin is a naturally occurring intracellular form of cobalamin and is more readily absorbed and retained longer than cyanocobalamin. It has been proposed that, in vivo, GluSCbl is an intermediate in the conversion of biologically inactive cyanocobalamin to the active coenzyme forms adenosylcobalamin (IV) and methylcobalamin (III). The reducing agent glutathione (GluSH) is required for the formation of GluSCbl, and is likely to be present in lower levels in AD patients compared with healthy individuals as a result of oxidative stress. Thus, GluSCbl has the potential to offer a valuable source of cobalamin in therapeutic applications requiring administration of a vitamin $B_{12}$ derivative.

GB 945722 (1964 to Merck & Co., Inc.) describes a method of preparing GluSCbl by reacting a 1:1 ratio hydroxocobalamin (hydroxycobalamin or aquocobalamin) and glutathione in water and precipitating the resulting complex to give a product of at least 95% purity. However, the technical sophistication available today for determining product purity was not available at the time of this earlier work and subsequent repeated attempts of this work have identified that the resulting product is in fact of only 60–70% purity (see Reference Examples A and B).

More recently, other methods for preparing GluSCbl in high purity have been reported (Pezacka, E., et al, *Biochem. Biophys. Res. Commun.*, 1990, 169, 443; Brown K., et al, *Biochem.*, 1993, 32, 8421; Brasch N., et al, *Inorg. Chem.*, 1999, 76, 197) using a large excess of GluSH (5–12×), however, an additional chromatographic step is required to provide a product of 98% purity.

Thus, there exists a need for methods of preparing GluSCbl of an acceptable purity level which do not require the cost and effort of a chromatographic purification step, which also can be performed in the presence of air, and which presents a method leading to a commercially viable process for the synthesis of glutathionylcobalamin.

SUMMARY OF THE INVENTION

It has now been found that the use of a relatively small excess of GluSH provides GluSCbl in acceptable purity without the need for an additional chromatographic purification step. Additionally, it has been found that the reaction can be run to an acceptable level of purity by using very high concentrations of the reactants, i.e. around saturation concentrations for aquocobalamin. One explanation for the process in accordance with the invention is that the relative concentrations of the reactants are manipulated in order to push the reaction toward the formation of product and to minimize the amount of oxidized glutathion (GluSSGlu) in the product. The $B_{12}$ catalyzed aerial oxidation of GluSH to GluSSGlu is well known, and this reaction lowers the yield and purity of the desired product. These methods may work in the alternative, so that a lower relative excess of GluSH may be used at higher concentrations of the reactants, or a higher relative excess of GluSH can be used at more normal concentrations of the reactants, with the caveat that the acceptable excess of GluSH is limited to less than 4 molar equivalents of GluSH per molar equivalent of hydroxycobalamin.

Accordingly, the invention provides a method for preparing glutathionylcobalamin (GluSCbl) comprising the steps of:
a) reacting a salt of hydroxycobalamin with from greater than 1 to less than 4 molar equivalents of glutathione (GluSH) in an aqueous solvent;
b) precipitating the formed GluSCbl from the aqueous solvent, optionally by the addition of a precipitate inducing solvent;
c) collecting the precipitated GluSCbl.

In a preferred embodiment of the invention, the reaction is carried out with from 1.1 to about 2.5 equivalents of GluSH, more preferably from about 1.2 to about 2 equivalents. Further in an alternative embodiment, the amount of hydroxycobalamin approaches saturation in the aqueous solvent, or in yet again another alternative embodiment, the reaction is run with a slight excess of GluSH and a concentration of at least about 0.025M hydroxycobalamin in the aqueous solvent is used. The synthesis is carried out under red light only conditions.

DESCRIPTION OF THE PREFERRED EMBODIMENTS

Throughout this specification and the claims which follow, unless the context requires otherwise, the word "comprise" and variations such as "comprises" and "comprising" will be understood to imply the inclusion of a stated integer or step or group of integers but not the exclusion of any other integer or step or group of integers.

As used herein, a salt of hydroxycobalamin refers to a compound $H_2OCbl.X$ (or HOCbl.HX) wherein X is a counter anion such as a halide (particularly Cl⁻) or an Oacyl group such as $O\bar{A}c$.

GluSH is used in greater than 1 to less than about 4 equivalents, preferably less than about 3 equivalents. In a particularly preferred embodiment GluSH is used in about 1.1 to about 2.5 equivalents, such as about 1.2, 1.5 or about 2 equivalents.

The reaction may be carried out in the presence or absence of air (i.e. under nitrogen or argon), however, since excluding air requires additional precautional steps, it may be preferable to simply perform the reaction in the presence of air.

The reaction is performed in an aqueous solvent, being water alone or a mixture of water and a water miscible solvent (such as MeOH, EtOH, PrOH & BuOH). Preferably the aqueous solvent is water alone. Where the reaction is carried out in a mixture of water and water miscible solvent, the proportion of water to water miscible solvent may depend on the kinetics and/or thermodynamics of the reaction. The reaction mixture may also optionally contain additional agents such as buffers, for example, MES. GluSCbl is slightly light-sensitive, therefore, preferably, the reaction is carried out under red light only conditions.

The reaction may be performed at a temperature from 0° to about 60°. In a preferred form of the invention, the reaction may be carried out at ambient room temperature, such as from about 15° C. to about 30° C., for example about 20–25° C.

The reaction should be carried out using high concentrations of HOCbl.HX and glutathione. Control experiments have shown that $B_{12}$-catalyzed oxidation of glutathione to its disulphide form does occur in the presence of air; however, the fraction of glutathione oxidized during the reaction will be minimal if high concentrations of glutathione are used. Ideally, the reaction is performed at a concentration of at least about 0.025M, and more preferably about 0.03, 0.04, or 0.05M aquocobalamin. Specifically, this reaction is run at a higher concentration of aquocobalamin than normal (at least about 0.04M or higher), and preferably at a concentration higher than about 50% of saturation, more preferably about 75% of saturation, and most preferably at a concentration of least about 90%, or even 95% of saturation. The reaction is allowed to proceed for a time sufficient to achieve substantial completion. Reference to substantial completion of the reaction is intended to refer to the substantial consumption (e.g. greater than 95%) of the HOCbl.HX.

Precipitation of the GluSCbl may be performed under cooling, for example ice cooling, eg to about −10–10° C. However, yield of the GluSCbl product can be increased by the addition of a precipitate inducing solvent. The precipitate inducing solvent used to precipitate the formed GluSCbl, which is preferably a water miscible solvent less polar then water and includes alcohols (such as MeOH, EtOH, PrOH & BuOH) and acetone, is added in an amount sufficient to induce precipitation of the formed GluSCbl. A preferred precipitate inducing solvent is acetone.

Preferred methods of the invention provide a final product with greater than 90% purity, preferably greater than about 95% purity, more preferably 97, 98 or 99% purity as determined by the any of methods described herein.

In a preferred form of the invention, the precipitated GluSCbl is collected by filtration, preferably under suction, and optionally washing the precipitate with a suitable solvent or mixture of solvents such as acetone and/or ether. In another embodiment of the invention, the precipitate can be collected by decanting off the solvents or removing them by suction. Preferably, the precipitate is further dried to remove any remaining solvent. This may be carried out by under vacuum, optionally with heating (at a temperature which does not decompose the GluSCbl, for example from about 25–40° C.).

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

The invention will now be described with reference to the following Examples which are intended for the purpose of illustration only and are not intended to limit the generality hereinbefore described.

EXAMPLES

Materials and Methods

Hydroxycobalamin hydrochloride (HOCbl.HCl, 98% (stated purity by manufacturer) was purchased from Fluka. The percentage of water in HOCbl.HCl (.nH$_2$O) (12±2%) was determined by converting HOCbl.HCl to (CN)$_2$Cbl$^-$ and the concentration of (CN)$_2$Cbl$^-$ determined by UV-vis spectroscopy (Barker, H. A.; Smyth, R. D.; Weissbach, H; Toohey, J. I.; Ladd, J. N.; Volcani, B. E. *J. Biol. Chem.*, 1960, 235, 480). Glutathione (GluSH, 98%; i.e., in its reduced form) was purchased from Aldrich.

$^1$H NMR spectra were recorded on an Inova 500 MHz spectrometer equipped with a 5 mm thermostatted (25.0±0.2° C.) probe. All solutions were prepared in D$_2$O and TSP (3-(trimethylsilyl)propionic-2,2,3,3-d$_4$ acid, sodium salt) was used as an internal standard. Visible spectra were recorded on a Cary 1E spectrophotometer equipped with a thermostatted cell changer (25.0±0.1° C.) and operated with WinUV Bio software (version 2.00).

Determination of the Purity of Cobalamins by the (CN)$_2$Cbl$^-$ Method

All cobalamin derivatives are converted to (CN)$_2$Cbl$^-$ by the addition of excess CN$^-$ (Pratt, J. M. (ed.) *Inorganic Chemistry of Vitamin B$_{12}$*; Academic Press: London, 1972). The concentration of (CN)$_2$Cbl$^-$ was determined by UV-vis spectroscopy. The purity represents the % of B$_{12}$ compounds (in this case GluSCbl or H$_2$OCbl$^+$) in the precipitated product. The experiment therefore indicates whether any GluSH (or GluSSGlu is present in the product.

Determination of the Purity of Cobalamins by the $^1$H NMR Method $^1$H NMR spectroscopy is a useful method to characterize and quantitate cobalamin species, since the NMR signals are unique for each cobalamin in the aromatic region (Brasch, N. E.; Finke, R. G. *J. Inorg. Biochem.*, 1999, 73, 215). This method therefore indicates the % of GluSCbl compared with other B$_{12}$ compounds (i.e H$_2$OCbl$^+$) in the product.

Reference Example A

HOCbl.HCl and glutathione (reduced) were dried under vacuum (<0.01 Pa) for 16 hr at room temperature. 401.8 mg (2.90×10$^{-4}$ moles) of HOCbl.HCl and 70.11 mg (2.28×10$^{-4}$ moles) of glutathione were dissolved in 30 mL of distilled water and the solution was stirred. The solution was heated to 60° C. and then hot acetone was added to make the volume of the solution 250 ml. The flask was removed from the heat and allowed to cool for 6 hr. The precipitate that had formed was collected by vacuum filtration, washed with acetone and allowed to dry in the air.

By the $^1$H NMR method, the GluSCbl product was found to contain 36% H$_2$OCbl$^+$. By the (CN)$_2$Cbl$^-$ method, the GluSCbl products was found to contain 11% glutathione.

Reference Example B

The procedure was repeated using HOCbl.HCl and glutathione that had not been dried in vacuo. 402.07 mg (2.56×10$^{-4}$ moles (12% H$_2$O)) of HOCbl.HCl and 70.20 mg (2.28×10$^{-4}$ moles) of glutathione were used.

By the $^1$H NMR method, the GluSCbl product was found to contain 28% H$_2$OCbl$^+$. By the (CN)$_2$Cbl$^-$ method, the GluSCbl product was found to contain 7% glutathione.

Example 1

(1.93 Equivalents of GluSH)

The hydrochloride salt of hydroxycobalamin, HOCbl.HCl (81.13 mg, 5.16×10$^{-5}$ moles (12% H$_2$O)) was dissolved in distilled water (0.800 ml) in a vial with gentle heating i.e. using a heat gun on a low setting. At these concentrations the solution is an intense red color and quite thick in appearance. After the addition of 0.382 ml of GluSH (0.261 M, 9.97×10$^{-5}$ moles), the vial was capped, vigorously shaken and left in the dark for 3 hr. A purple precipitate formed upon the addition of 1.00 ml acetone. After cooling in an ice bath for 30 min, the purple precipitate was filtered under suction (water aspirator), washed with acetone and ether and dried at 50° C. for 2 days under vacuum (0.13 mbar). Yield 63.6 mg (78%). Duplicate syntheses gave yields of 76 and 86%.

The product was characterized by $^1$H NMR and UV-vis spectroscopies, EI-MS and the (CN)$_2$Cbl$^-$ method. $^1$H NMR signals of GluSCbl in the aromatic region (pD 5.5, 0.100 M MES buffer; MES=(2-[N-morpholino]ethanesulfonic acid)), referenced internally with TSP, 25.0° C.: δ 7.20, 6.95, 6.40, 6.29(d) and 6.11 ppm (in excellent agreement with literature values (Brasch, N. E.; Hsu, T.-L. C.; Doll, K. M.; Finke, R. G. *J. Inorg. Biochem.*, 1999, 76, 197). A value of 99±1% GluSCbl purity was determined by integration of the $^1$H NMR signals in the aromatic region. UV-visible $\lambda_{max}$ ($\epsilon$, M$^{-1}$ cm$^{-1}$, in H$_2$O, 25.0° C.): 252 (2.07×10$^4$), 288 (2.38×10$^4$), 334 (1.59×10$^{-4}$), 372 (1.40×10$^4$), 428 (4.25×10$^3$) and 534 (7.97×10$^3$) nm. The values are similar to previously reported values for GluSCbl (Brasch, N. E.; Hsu, T.-L. C.; Doll, K. M.; Finke, R. G. *J. Inorg. Biochem.*, 1999, 76, 197). The percentage of species other than cobalamins which were present in the product was determined by converting the product to (CN)$_2$Cbl$^-$ and found to be 2±1%. EI-MS (positive ion mode, in MeOH): calc. molecular mass for C$_{72}$H$_{105}$O$_{20}$N$_{10}$PSCo (ie [M+H])=1635.648; found: 1635.5 ([M+H]) and 1329.5 [(M+H)–GluS]$^-$ where M=[(GluH)SH$^-$)Cbl].

Example 2

(1.93 Equivalents of GluSH)

The same method as for Example 1 was performed (2×) using identical quantities of reagents by another person.

81.13 mg HOCbl.HCl (5.16×10$^{-5}$ moles (12% H$_2$O)) in 0.800 ml H$_2$O 0.382 ml of 0.261 M GluSH (9.97×10$^{-5}$ moles)

1.00 ml acetone added

Yield: 68.3 mg (81%) and 59.9 mg (71%)

Purity: 99% and 99% by $^1$H NMR method 99% and 99% by (CN)$_2$Cbl$^-$ method

Example 3

(1.16 Equivalents of GluSH)

The same method as for Example 1 was performed using the following quantities of reagents and solvents.

81.26 mg HOCbl.HCl ($5.17 \times 10^{-5}$ moles (12% $H_2O$)) in 0.800 ml $H_2O$
0.240 ml of 0.25 M GluSH ($6.00 \times 10^{-5}$ moles)
1.00 ml acetone added
Yield 63.5 mg (75%)
Purity: 92% by $^1H$ NMR method
97% by $(CN)_2Cbl^-$ method

Example 4

(4.79 Equivalents of GluSH)

The same method as for Example 1 was performed using the following quantities of reagents and solvents.

81.61 mg HOCbl.HCl ($5.22 \times 10^{-5}$ moles (12% $H_2O$)) in 0.800 ml $H_2O$
1.000 mL of 0.250 M GluSH ($2.50 \times 10^{-4}$ moles)
1.00 ml acetone added
No crystals, only an oil was formed.

Example 5

(4.67 Equivalents of GluSH)

The same method as for Example 1 was performed using the following quantities of reagents and solvents.

41.90 mg HOCbl.HCl ($2.68 \times 10^{-5}$ moles (12% $H_2O$)) in 0.400 ml $H_2O$
0.500 mL of 0.250 M GluSH ($1.25 \times 10^{-4}$ moles)
1.00 ml acetone added
Yield: 4.68 mg (11%)
Purity: 53% by $(CN)_2Cbl^-$ method. Insufficient product to determine purity by $^1H$ NMR method.

While in accordance with the patent statutes, the best mode and preferred embodiment have been set forth, the scope of the invention is not limited thereto, but rather by the scope of the attached claims.

What is claimed is:

1. A method for preparing glutathionylcobalamin (GluSCbl) comprising the steps of:
   a) reacting a salt of hydroxycobalamin with from greater than one to less than 4 molar equivalents of glutathione (GluSH) in an aqueous solvent;
   b) precipitating the formed GluSCbl from the aqueous solvent, optionally by the addition of a precipitate inducing solvent;
   c) collecting the precipitated GluSCbl.

2. A method according to claim 1 wherein from about 1.1 to 3.0 equivalents of GluSH are used.

3. A method according to claim 2 wherein from about 1.2 to 2.0 equivalents of GluSH are used.

4. A method according to claim 1 wherein the salt of hydroxycobalamin is $H_2OCbl.Cl$ or $H_2OCbl.OAc$.

5. A method according to claim 1 wherein the aqueous solvent is water.

6. A method according to claim 1 wherein the precipitate inducing solvent is acetone.

7. A method according to claim 1 wherein the precipitate is collected by filtration.

8. A method according to claim 1 where the obtained GluSCbl has a purity of at least 95% as determined by the $^1H$ NMR method and/or $(CN)_2Cbl^-$ method.

9. A method according to claim 1 wherein the reaction is carried out at a concentration in the range of 0.001 to 0.1 M HOCbl.HX, wherein X is a counter anion selected from the group consisting of halide, Cl, or OAc.

10. A method for preparing glutathionylcobalamin (GluSCbl) comprising the steps of:
    a) reacting a salt of hydroxycobalamin at a concentration within at least about 75% of its saturation limit, with at least one equivalent of glutathione (GluSH) in an aqueous solvent;
    b) precipitating the formed GluSCbl from the aqueous solvent by the addition of a precipitate inducing solvent;
    c) collecting the precipitated GluSCbl.

11. A method according to claim 10 wherein from about 1.1 to 4.0 equivalents of GluSH are used.

12. A method according to claim 11 wherein from about 1.2 to 2.0 equivalents of GluSH are used.

13. A method according to claim 12 wherein the salt of hydroxycobalamin is $H_2OCbl.Cl$ or $H_2OCbl.OAc$.

14. A method according to claim 10 wherein the aqueous solvent is water.

15. A method according to claim 10 wherein the precipitate inducing solvent is acetone.

16. A method according to claim 10 wherein the precipitate is collected by filtration.

17. A method according to claim 10 where the obtained GluSCbl has a purity of at least 95% as determined by the $^1H$ NMR method and/or $(CN)_2 Cbl^-$ method.

18. A method according to claim 1 wherein the reaction is carried out at a concentration in the range of 0.001 to 0.1 M HOCbl.HX, wherein X is a counter anion selected from the group consisting of halide, Cl, or OAc.

* * * * *